United States Patent
Wang et al.

(10) Patent No.: US 11,402,284 B2
(45) Date of Patent: Aug. 2, 2022

(54) APPARATUS AND METHOD FOR MEASURING TOE FLEXION AND EXTENSION

(71) Applicant: The Board of Regents of the University of Oklahoma, Norman, OK (US)

(72) Inventors: Hongwu Wang, Edmond, OK (US); Elizabeth Hile, Edmond, OK (US); Mustafa Ghazi, Norman, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 25 days.

(21) Appl. No.: 16/915,956

(22) Filed: Jun. 29, 2020

(65) Prior Publication Data
US 2020/0408622 A1    Dec. 31, 2020

Related U.S. Application Data

(60) Provisional application No. 62/867,844, filed on Jun. 27, 2019.

(51) Int. Cl.
*G01L 5/00* (2006.01)
*A63B 23/10* (2006.01)

(52) U.S. Cl.
CPC ............ *G01L 5/0028* (2013.01); *A63B 23/10* (2013.01); *A63B 2220/51* (2013.01)

(58) Field of Classification Search
CPC .... G01L 5/0028; A63B 23/10; A63B 2220/51
See application file for complete search history.

(56) References Cited

U.S. PATENT DOCUMENTS 3,782,743 A * 1/1974 Sittmann ............ A63C 9/08557
                                                    280/630
3,861,205 A * 1/1975 Frey ..................... A63C 11/265
                                                    73/862.02

(Continued)

FOREIGN PATENT DOCUMENTS

JP    2002360550 A    12/2002
JP    2007044495 A    2/2007

(Continued)

OTHER PUBLICATIONS

Bruening, D.A., Ridge, S.T., Jacobs, J.L., Olsen, M.T., Griffin, D.W., Ferguson, D.H., Bassett, K.E., and Johnson, A.W. Functional assessments of foot strength: a comparative and repeatability study. BMC Musculoskelet Disord, 2019, 20:608.

(Continued)

*Primary Examiner* — Max H Noori
*Assistant Examiner* — Masoud H Noori
(74) *Attorney, Agent, or Firm* — Crowe & Dunlevy, P.C.

(57) ABSTRACT

A toe dynamometer is configured to accurately and precisely measure toe extensor strength. The toe dynamometer includes a platform configured to accommodate a patient's foot, and a sensor assembly comprising a force sensor and a toe cap connected to the force sensor. The force sensor is configured to measure forces applied to the force sensor by toe flexion on the force sensor and from toe extension away on the force sensor through the toe cap.

20 Claims, 6 Drawing Sheets

(56) References Cited

U.S. PATENT DOCUMENTS

| | | | | |
|---|---|---|---|---|
| 4,128,257 A | * | 12/1978 | Zoor | A63C 9/0807 |
| | | | | 280/614 |
| 5,498,017 A | * | 3/1996 | Rohrmoser | A63C 9/0802 |
| | | | | 280/612 |
| 9,675,491 B1 | * | 6/2017 | Seaman | A61F 5/019 |
| 2017/0086751 A1 | | 3/2017 | Amos et al. | |

FOREIGN PATENT DOCUMENTS

| | | |
|---|---|---|
| JP | 3144141 U | 8/2008 |
| JP | 2006006369 A | 7/2010 |
| JP | 2016022362 A * | 2/2016 |

OTHER PUBLICATIONS

Garofolini, A., Taylor, S., McLaughlin, P., Stokes, R., Kusel, M., and Mickle, K. Repeatability and accuracy of a foot muscle strength dynamometer. Med Eng Phys, 2019, 67: 102-108.

Ridge, S.T., Myrer, J.W., Olsen, M.T., Jurgensmeier, K., and Johnson, A.W. Reliability of doming and toe flexion testing to quantify foot muscle strength. J Foot Ankle Res, 2017, 10:55.

Soysa, A., Hiller, C., Refshauge, K., and Burns, J. Importance and challenges of measuring intrinsic foot muscle strength. J Foot Ankle Res, 2012, 5:29.

Spink, M.J., Fotoohabadi, M.R., and Menz, H.B. Foot and ankle strength assessment using hand-held dynamometry: reliability and age-related differences. Gerontology, 2010, 56: 525-532.

Suwa, M., Imoto, T., Kida, A., Iwase, M., and Yokochi, T. Age-related reduction and independent predictors of toe flexor strength in middle-aged men. J Foot Ankle Res, 2017, 10:15.

* cited by examiner

APPARATUS AND METHOD FOR MEASURING TOE FLEXION AND EXTENSION

RELATED APPLICATIONS

The present application claims the benefit of U.S. Provisional Patent Application Ser. No. 62/867,844 filed Jun. 27, 2019 entitled, "Apparatus for Measuring Toe Flexion and Extension," the disclosure of which is herein incorporated by reference.

BACKGROUND

Toe strength and range of motion may be used to diagnose or evaluate a number of conditions, including cancer, diabetes, vascular disease, and distal neuropathies or myopathies of any etiology. In the past, physical therapists, oncologists, neurologists and other healthcare providers have used manual examination techniques and handheld dynamometers to evaluate patients' toe strength and range of motion. Manual examination methods are inherently subjective and prone to discrepancies between clinicians. Although handheld dynamometers are capable of producing more consistent results, the manner in which the handheld dynamometers are used introduces significant variability.

In particular, the output from handheld dynamometers is impacted by variability in limb stabilization and foot positioning, as well as the precise location and intensity of resistance applied by the examiner holding the dynamometer against the patient. Additionally, patients with neuropathic or myopathic weakness often have strength falling below the levels that are needed to be accurately measured by these tools, which require an isometric hold against an externally-applied force. In these situations, the patient's toe immediately 'breaks' from the hold position even though a wide range of force output might otherwise be measured. Capturing strength in these lower but still discernable ranges is important for tracking distal neuropathic or myopathic processes so that treatment or referral decisions can be made.

There is, therefore, a need for an improved mechanism for evaluating toe strength and range of motion. The present disclosure is directed to addressing these and other deficiencies in the prior art.

BRIEF DESCRIPTION OF THE DRAWINGS

The accompanying drawings, which are incorporated in and constitute a part of this specification, illustrate one or more implementations described herein and, together with the description, explain these implementations. The drawings are not intended to be drawn to scale, and certain features and certain views of the figures may be shown exaggerated, to scale or in schematic in the interest of clarity and conciseness. Not every component may be labeled in every drawing. Like reference numerals in the figures may represent and refer to the same or similar element or function.

DETAILED DESCRIPTION

Figure 1:
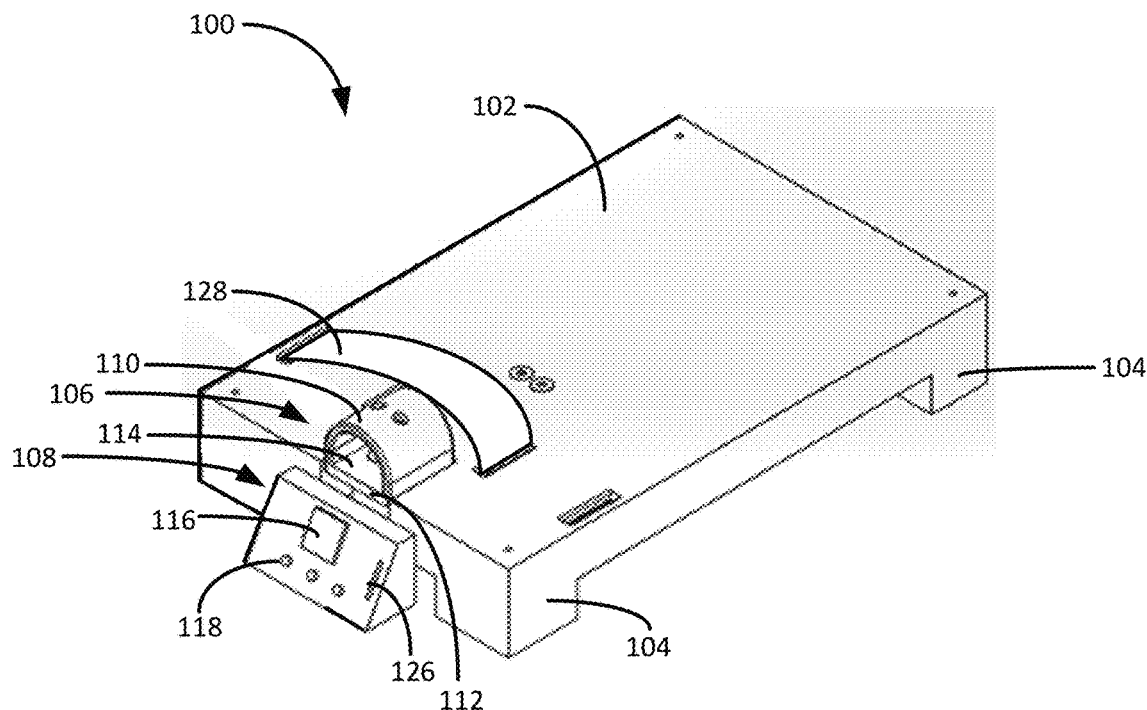
FIG. 1 is a top perspective view of a toe dynamometer constructed in accordance with exemplary embodiments.

The present disclosure is directed, in non-limiting embodiments, to a toe dynamometer configured to accurately and precisely measure toe extensor strength. In some embodiments, the toe dynamometer includes a platform configured to accommodate a patient's foot, and a sensor assembly comprising a force sensor and a toe cap connected to the force sensor. The force sensor is configured to measure forces applied to the force sensor by toe flexion on the force sensor and from toe extension away on the force sensor through the toe cap. In other embodiments, the toe dynamometer includes a platform configured to accommodate a patient's foot, a sensor assembly and a control module connected to the sensor assembly. The sensor assembly has a force sensor and a toe cap connected to the force sensor. The force sensor is configured to measure forces applied to the force sensor by toe flexion on the force sensor and from toe extension away on the force sensor through the toe cap. In yet another embodiment, the toe dynamometer has a platform configured to accommodate a patient's foot and a sensor assembly that has a force sensor and a toe cap connected to the force sensor. The force sensor is configured to measure forces applied to the force sensor by toe flexion on the force sensor and from toe extension away on the force sensor through the toe cap and produce output signals representative of the magnitude and direction of the forces applied by toe flexion and toe extension over time.

Other non-limiting embodiments include a method for measuring a patient's toe extensor function with the toe dynamometer during a measurement session. The method begins with the step of securing the patient's toe within a sensor assembly on the toe dynamometer where the sensor assembly has a force sensor and a toe cap connected to the force sensor, where the force sensor is under the patient's toe and the toe cap is above the patient's toe. Next, the method includes the step of instructing the patient to execute a measurement protocol that includes toe flexion exercises, toe extension exercises, or a combination of toe flexion and toe extension exercises. The method also includes the step of recording in real time the force measurements resulting from the application of force by the patient's toe on the force sensor during the measurement protocol.

Before describing various embodiments of the present disclosure in more detail by way of exemplary description, examples, and results, it is to be understood as noted above that the present disclosure is not limited in application to the details of methods and apparatus as set forth in the following description. The present disclosure is capable of other embodiments or of being practiced or carried out in various ways. As such, the language used herein is intended to be given the broadest possible scope and meaning; and the embodiments are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the disclosure. However, it will be apparent to a person having ordinary skill in the art that the embodiments of the present disclosure may be practiced without these specific details. In other instances, features which are well known to persons of ordinary skill in the art have not been described in detail to avoid unnecessary complication of the description.

Unless otherwise defined herein, scientific and technical terms used in connection with the present disclosure shall have the meanings that are commonly understood by those having ordinary skill in the art. Further, unless otherwise required by context, singular terms shall include pluralities and plural terms shall include the singular.

All patents, published patent applications, and non-patent publications mentioned in the specification are indicative of the level of skill of those skilled in the art to which the present disclosure pertains. All patents, published patent applications, and non-patent publications referenced in any portion of this application are herein expressly incorporated by reference in their entirety to the same extent as if each individual patent or publication was specifically and individually indicated to be incorporated by reference.

As utilized in accordance with the methods and apparatus of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

As used herein, all numerical values or ranges (e.g., in units of length such as micrometers or millimeters) include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth. Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-1,000, includes ranges of 1-20, 10-50, 50-100, 100-500, and 500-1,000, for example.

As used herein, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the terms "about" or "approximately" are used to indicate that a value includes the inherent variation of error. Further, in this detailed description, each numerical value (e.g., temperature or time) should be read once as modified by the term "about" (unless already expressly so modified), and then read again as not so modified unless otherwise indicated in context. As noted above, any range listed or described herein is intended to include, implicitly or explicitly, any number within the range, particularly all integers, including the end points, and is to be considered as having been so stated. For example, "a range from 1 to 10" is to be read as indicating each possible number, particularly integers, along the continuum between about 1 and about 10. Thus, even if specific data points within the range, or even no data points within the range, are explicitly identified or specifically referred to, it is to be understood that any data points within the range are to be considered to have been specified, and that the inventors possessed knowledge of the entire range and the points within the range. Unless otherwise stated, the term "about" or "approximately", where used herein when referring to a measurable value such as an amount, length, thickness, a temporal duration, and the like, is meant to encompass, for example, variations of ±20% or ±10%, or ±5%, or ±1%, or ±0.1% from the specified value, as such variations are appropriate to perform the disclosed methods and as understood by persons having ordinary skill in the art.

As used herein, the term "substantially" means that the subsequently described parameter, event, or circumstance completely occurs or that the subsequently described parameter, event, or circumstance occurs to a great extent or degree. For example, the term "substantially" means that the subsequently described parameter, event, or circumstance occurs at least 90% of the time, or at least 91%, or at least 92%, or at least 93%, or at least 94%, or at least 95%, or at least 96%, or at least 97%, or at least 98%, or at least 99%, of the time, or means that the dimension or measurement is within at least 90%, or at least 91%, or at least 92%, or at least 93%, or at least 94%, or at least 95%, or at least 96%, or at least 97%, or at least 98%, or at least 99%, of the referenced dimension or measurement (e.g., length).

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Where applicable, although state diagrams, flow diagrams or both may be used to describe embodiments, the present disclosure is not limited to those diagrams or to the corresponding descriptions. For example, flow need not move through each illustrated box or state, or in exactly the same order as illustrated and described. Methods of the present disclosure may be implemented by performing or completing manually, automatically, or a combination thereof, selected steps or tasks. The term "method" may refer to manners, means, techniques and procedures for accomplishing a given task including, but not limited to, those manners, means, techniques and procedures either known to, or readily developed from known manners, means, techniques and procedures by practitioners of the art to which the invention belongs.

It should be noted that where reference is made herein to a method comprising two or more defined steps, the defined steps can be carried out in any order or simultaneously (except where context excludes that possibility), and the method can also include one or more other steps which are carried out before any of the defined steps, between two of the defined steps, or after all of the defined steps (except where context excludes that possibility). Still further, additional aspects of the various embodiments of the instant disclosure may be found in one or more appendices attached hereto and/or filed herewith, the disclosures of which are incorporated herein by reference as if fully set out at this point.

Figure 2:
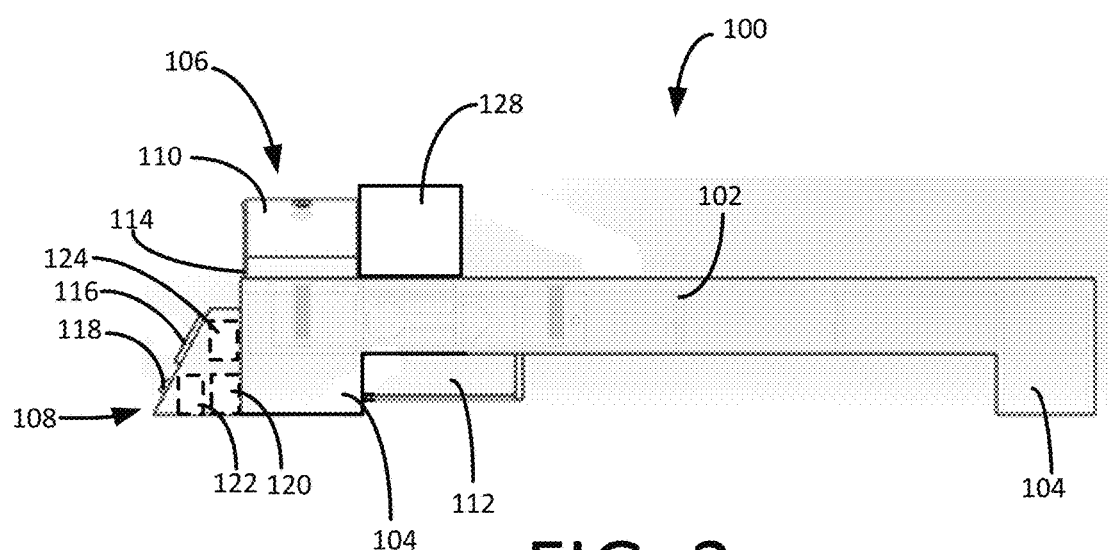
FIG. 2 is a side view of the toe dynamometer of FIG. 1.
Figure 3:
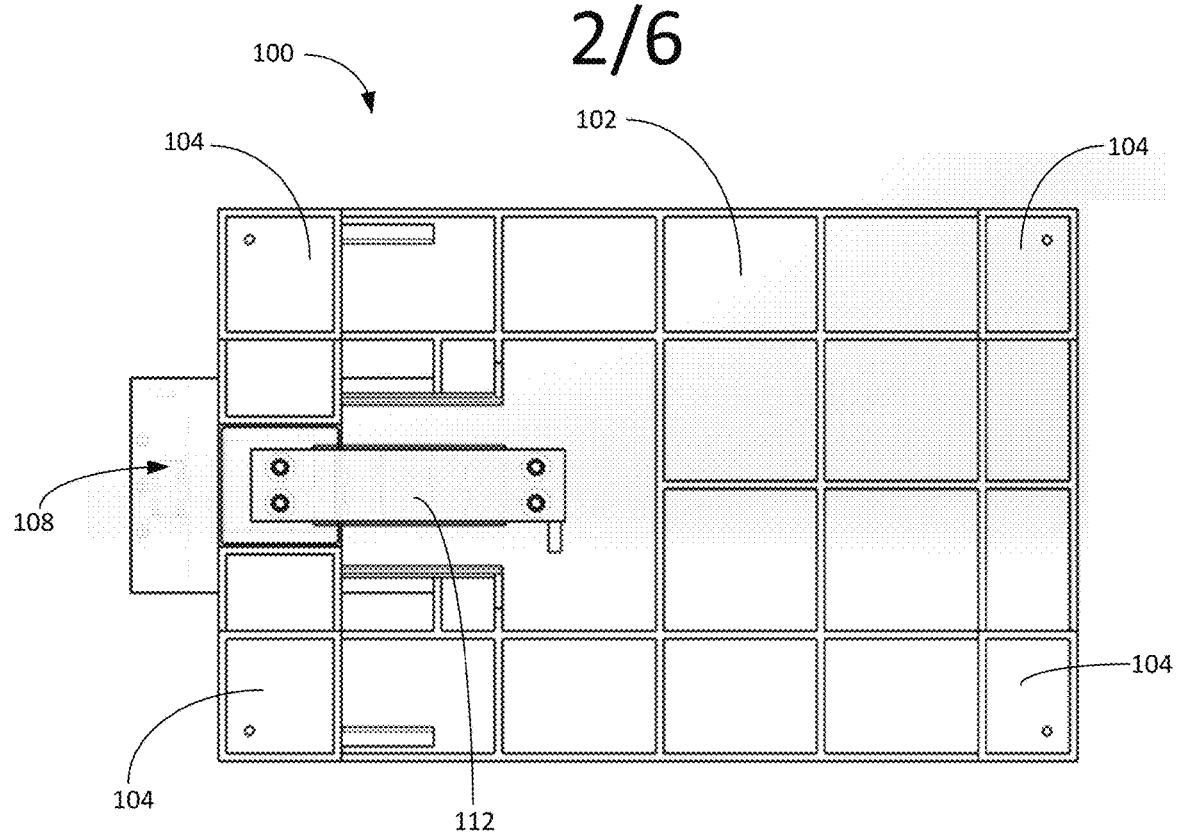
FIG. 3 is a bottom view of the toe dynamometer of FIG. 1.

Referring now to FIGS. 1-3, shown therein are top perspective, side and bottom views, respectively, of a toe dynamometer 100. The toe dynamometer 100 has a platform 102 with a plurality of feet 104 that support the base 102 on a floor or other surface. The toe dynamometer 100 includes a sensor assembly 106 and an onboard control panel 108. In the embodiment depicted in FIG. 1, the platform 102 is sized and configured to accommodate a patient's left or right foot such that the first toe (sometimes referred to as the "big toe," "great toe" or "hallux") on either foot can be easily placed within the sensor assembly 106 that is centrally located proximate to an edge of the platform 102.

The sensor assembly 106 is retained within the platform 102 and includes a toe cap 110 connected to a force sensor 112. The force sensor 112 is substantially flush with the top surface of the platform 102. In some embodiments, the force sensor 112 is a load cell that is configured to measure the magnitude and direction of a force applied to the surface of the load cell, and output a responsive sensor output signal. The toe cap 110 can be constructed from a rigid or semi-rigid material, or from a flexible fabric or synthetic material that can be tightened around a patient's toe. In exemplary embodiments, the toe cap 110 is configured to be easily exchanged so that various sizes and types of toe caps 110 can be quickly connected to the force sensor 112 to accommodate variations in patient anatomy. The toe cap 110 is preferably adjusted such that there is little or no space between the top of the patient's first toe and the inside of the toe cap 110 when the patient's toe is planted in a neutral position on the force sensor 112. This ensures that the entire range of movement of the patient's toe is detectable by the sensor assembly 106.

In exemplary embodiments, the force sensor 112 is an electronic load cell or scale that has a sensor surface 114 to which the toe cap 110 is connected. The force sensor 112 is configured to measure and report both the magnitude and direction of the force applied to the sensor assembly 106. If force is applied against the sensor surface 114 during toe flexion, the force sensor 112 measures and reports the magnitude of the force in a positive direction. If the toe cap 110 is pulled away from the force sensor 112 during toe extension, the force sensor 112 measures and reports the magnitude of force in a negative direction. In both cases, the force sensor 112 measures the magnitude and direction of force in real time with a sampling rate that permits multiple measurements to be taken over a short period of time (e.g., 100 measurements/second). In some embodiments, the sampling rate, the sampling time duration, and corresponding data file size can be adjusted by the clinician with the control panel 108.

The sensor output signal is provided to the control panel 108 for interpretation, processing and display. The control panel 108 includes a display 116, control buttons 118, a battery 120, a processor 122, memory 124, and an output module 126. The display 116 is configured to display the operational status of the toe dynamometer 100, the real-time measurements from the force sensor 112, charge levels in the battery 120, and other messages produced by the processor 122. It will be appreciated that the onboard display 116 is optional and not included in certain embodiments. The battery 120 is located inside the control panel 108 or elsewhere within the toe dynamometer 100. In some embodiments, the toe dynamometer 100 is configured to be powered by standard grid or wall power. The control buttons 118 may include a power button, a tare button, and a record button for initiating a recording session. Navigation buttons may be provided to cycle through menus, settings and data files stored within the memory 124. In some embodiments, the toe dynamometer 100 is configured to automatically power on when an initial force is measured by the force sensor 112. The toe dynamometer 100 can be configured to automatically power down after the passage of a predetermined period without the detection of a load by the force sensor 112.

The output module 126 is configured to facilitate the exchange of information measured by the toe dynamometer 100. In one embodiment (depicted in FIG. 1), the output module 126 includes a card slot that is configured to accept a standard removable digital memory card (e.g., Secure Digital formatted cards). The memory card can be used to store and transfer measurement data from the toe dynamometer 100 to a computer. In another embodiment, the output module 126 includes a wired data port (e.g., USB port) to permit the direct transfer of data to and from the toe dynamometer 100 over a wired connection. In yet another embodiment, the output module 126 includes a wireless network adapter (e.g., WiFi or Bluetooth) that permits the exchange of information between the toe dynamometer 100 and a computer or network over a wireless connection. In yet other embodiments, the toe dynamometer 100 is provided with a printer configured to produce a printed report of the measurements taken and processed by the toe dynamometer 100. As used herein and in the appended claims, the term "output module" may refer to the display 116, a removable memory card slot, a printer, a wired data port, and a wireless network adapter.

In some embodiments, the toe dynamometer 100 is configured as a peripheral instrument that is operable only when connected to a computer, which receives the sensor output signals from the force sensor 112. In these embodiments, the toe dynamometer 100 may not include the onboard processing electronics such as the control panel 108, display 116, control buttons 118, a battery 120, a processor 122, and memory 124.

Figure 4:
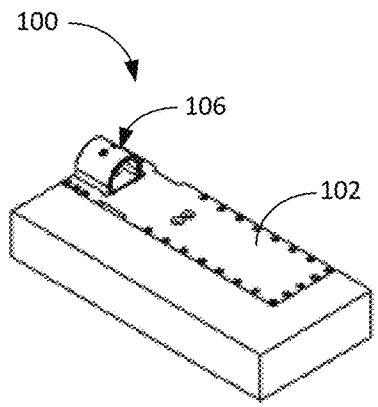
FIG. 4 is a top perspective view of another embodiment of the toe dynamometer configured for use with a patient's left foot.
Figure 5:
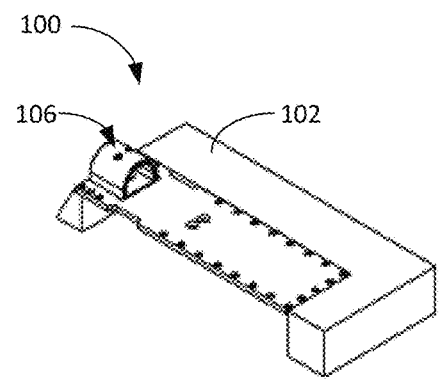
FIG. 5 is a top perspective view of another embodiment of the toe dynamometer configured for use with a patient's right foot.

The toe dynamometer 100 optionally includes a foot strap 128 that can be used to secure the patient's foot to the platform 102. The foot strap 128 can be used to prevent the patient's foot from moving to ensure that any movements detected by the force sensor 112 are isolated to the patient's toe. The foot strap 128 can be moved between positions on the platform 102 depending on whether the patient's left or right foot is being tested with the toe dynamometer 100. In contrast, the embodiments depicted in FIGS. 4 and 5 are each configured to independently accommodate the patient's left and right foot, respectively. In the embodiments depicted in FIGS. 4 and 5, the toe dynamometer 100 does not include the foot strap 128 and the platform feet 104 are incorporated into the platform 104. In these embodiments, the unneeded portion of the platform 102 can be configured to be folded under the portion of the platform 102 that supports the patient's foot during the examination.

Figure 6:
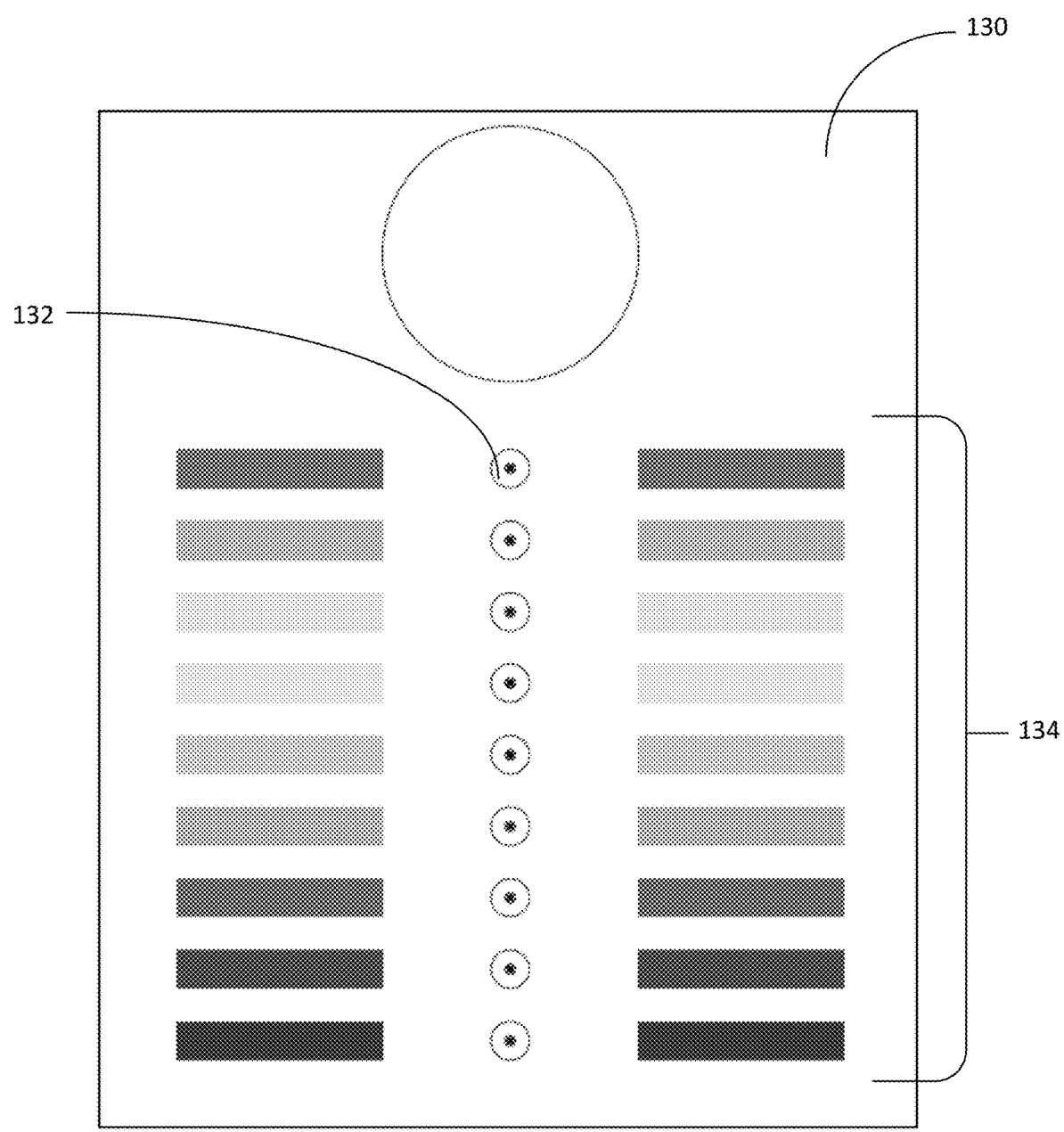
FIG. 6 is view of an embodiment of the display module configured to provide the patient with a real-time indication of the amount of force exerted by the patient.

Turning to FIG. 6, shown therein is an embodiment of the toe dynamometer 100 in which the display module 116 or a patient display module 130 is configured to provide the patient with real-time visual and audio feedback during a measurement session. In some embodiments, the patient display module 130 provides a large light-up display indicator with a nine LED lights 132 placed proximate to a series of color bands 138 that indicate a relative level of exertion. The number of LED lights 132 illuminated is proportional to the live force data from the sensor assembly 106. The stronger the force applied by the patient, the greater the number of lights 132 that are illuminated. The patient can be told to reach a specific light (force) level, or maintain a specific light (force) level. Any fluctuations in applied force are reflected in real time on the patient display module 130. The patient display module 130 can be tailored to custom force profiles depending on the patient requirements and abilities. The range of force expressed by the series of lights 134 can be adjusted to match the force output range of the particular patient. For example, for very weak patients, the force scale of the patient display module 130 can be adjusted such that the patient can more easily light up the entire series of lights 132. The patient display module 130 can also be programmed to flash and provide a visual cue of when to start.

In some embodiments, the patient display module 130 is also configured to provide audio feedback. Audio sounds or recordings from a therapist can be played by the toe dynamometer 100 to encourage the patient to apply or maintain a specific level of force. This ensures that the same words of encouragement are delivered to each patient. The start of the audio recording provides an auditory cue of when to start.

In one embodiment, a method of operation of the present disclosure begins by placing the toe dynamometer 100 on the floor or other stable surface. The clinician then assists the patient, as necessary, in placing the patient's foot on the platform 102 such that the patient's first toe is located under the toe cap 110. The toe cap 110 can be adjusted or exchanged to ensure a proper fit with the patient's first toe. The foot strap 128 can then be used to secure the patient's foot to the platform 102. Once the patient's foot and toe are secured within the toe dynamometer 100, the clinician can begin the examination (or measurement session) by taring the force sensor 112. Depending on the examination protocol, the clinician can then evaluate the patient's toe strength by asking the patient to perform toe flexion and toe extension maneuvers while the toe dynamometer 100 records the force applied through the force sensor 112. At the conclusion of the examination protocol, the clinician can release the patient's foot from the platform 102. The measurement data recorded by the toe dynamometer 100 can then be shared from the output module 126 for further analysis and diagnostics.

Figure 7:
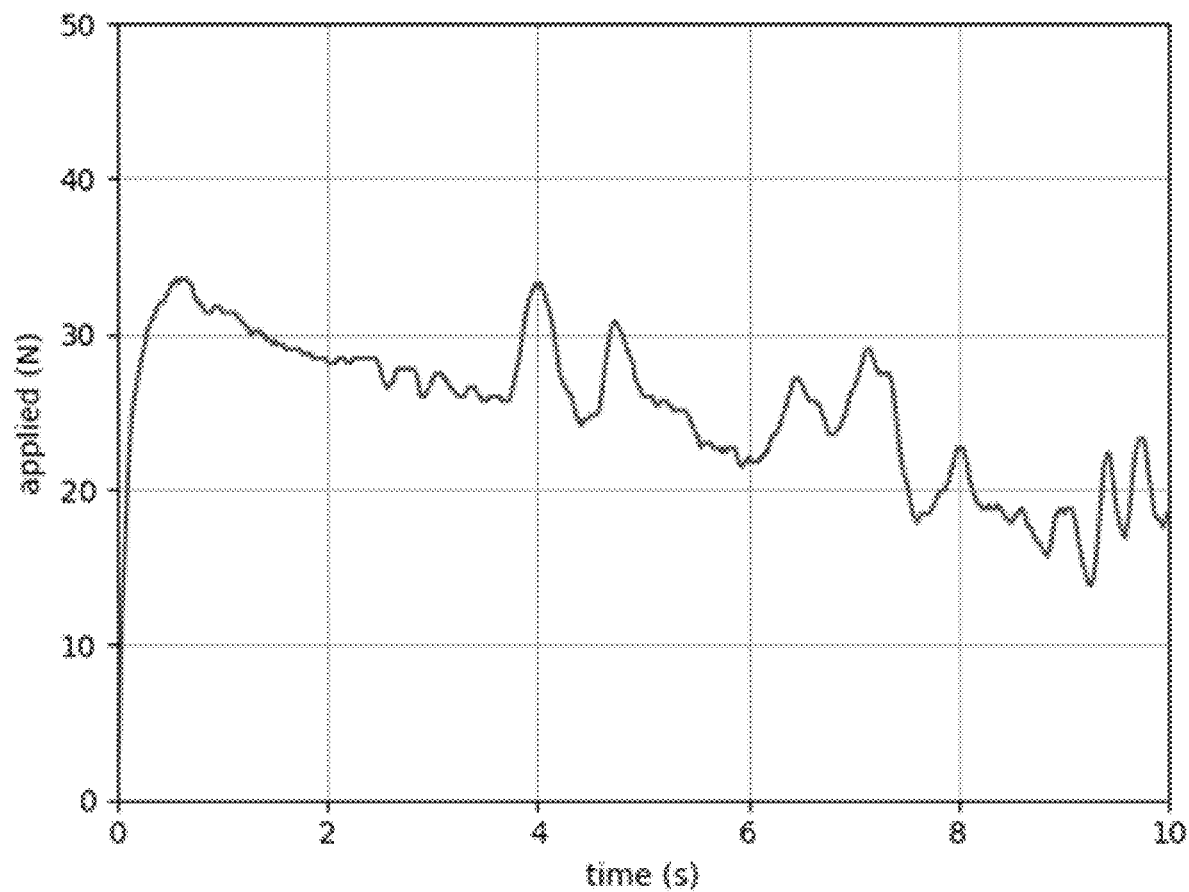
FIG. 7 is an example graph of the exertion of force (N) over time (s) using measurements taken by the toe dynamometer during a measurement session.
Figure 8:
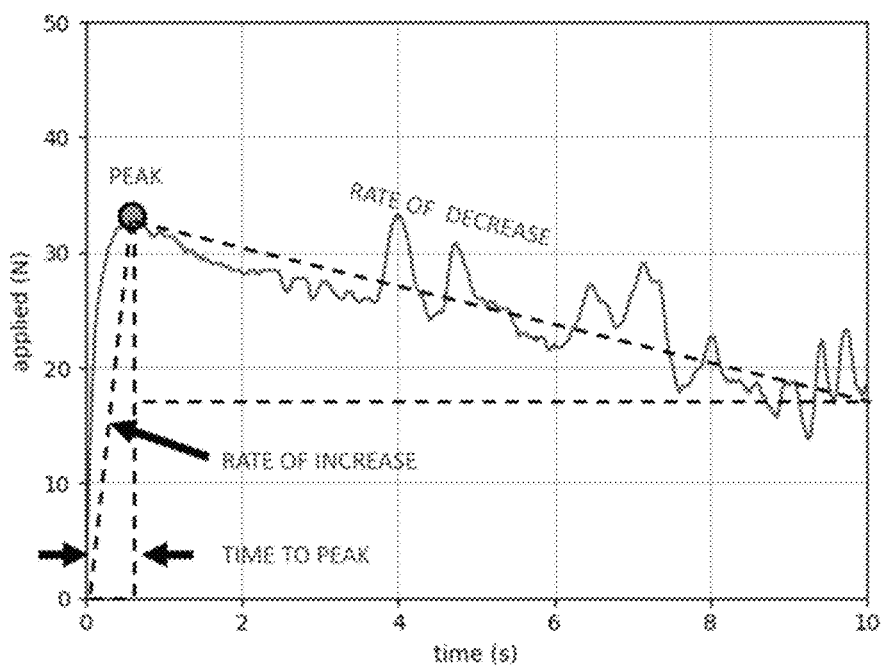
FIG. 8 is an example graph depicting the determination of several metrics based on the analysis of data recorded by the toe dynamometer.
Figure 9:
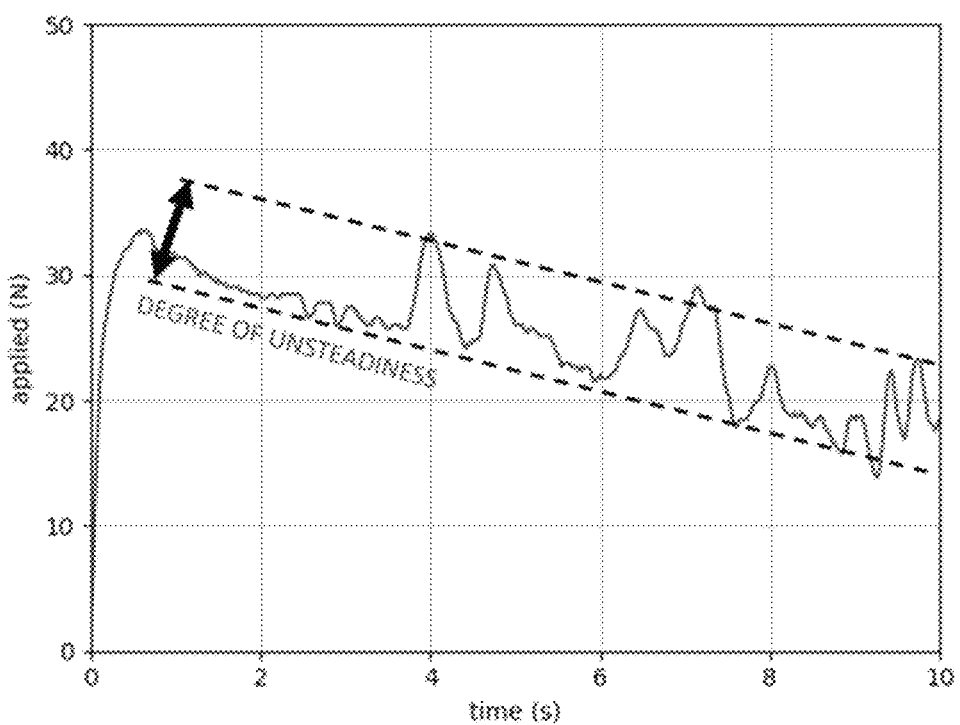
FIG. 9 is an example graph depicting the determination of an unsteadiness metric based on the analysis of data recorded by the toe dynamometer.

The toe dynamometer 100 is well suited to record the patient's ability to exert force over an extended period (for the functionally relevant estimation of muscle or nerve fatigue). A typical strength profile recorded by the toe dynamometer 100 is illustrated in FIG. 7, which plots the force exerted by the patient's tow on the force sensor 112 (in Newtons) over time (in seconds). The toe dynamometer 100 can be configured to analyze the data recorded during the measurement session and extract certain metrics or health indices based on the data recorded by the toe dynamometer 100. These metrics include, but are not limited to, peak strength, time to peak, rate of increase up to peak strength, and the rate of decrease after peak strength. These determinations are illustrated in FIG. 8 using the same measurements graphed in FIG. 7. The toe dynamometer 100 can also be configured to determine the degree of unsteadiness in strength profile, which is illustrated in FIG. 9 based on the same data recorded and displayed in FIG. 7. Various signal processing techniques and statistical methods may be used in compiling these metrics and indices.

Figure 10:
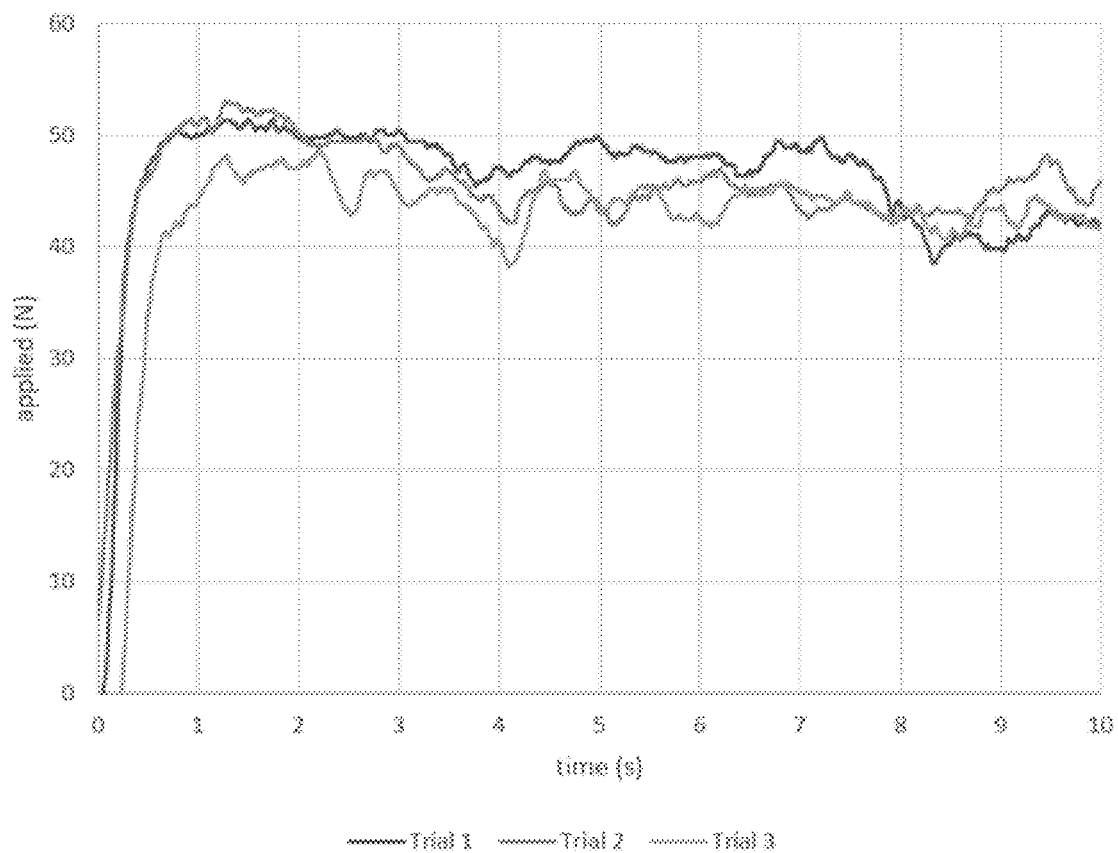
FIG. 10 depicts a comparative graph of multiple measurement sessions (trials) over time using the toe dynamometer.
Figure 11:
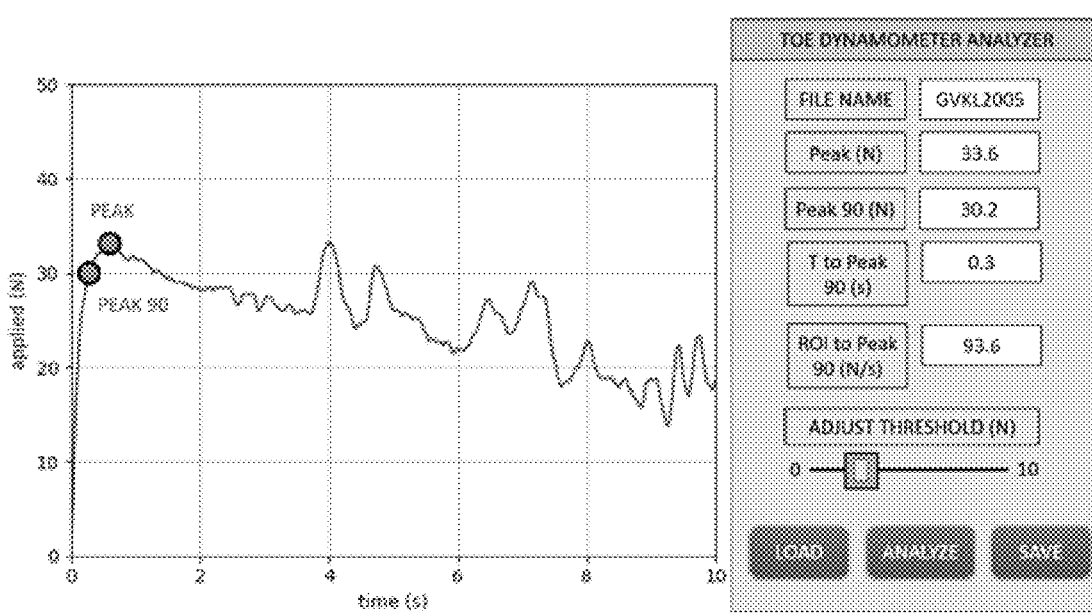
FIG. 11 depicts an example of the use of a custom analysis module within the toe dynamometer for evaluating and analyzing measurements made by the toe dynamometer.

The toe dynamometer 100 can also be configured to aggregate data from multiple measurement session profiles for easy reference and comparison, as illustrated in FIG. 10 for Trials 1-3. As noted above, the software to perform all these measurement, analytic and display functions may reside on the toe dynamometer 100 itself or on an external device such as a remote microcontroller board, a smart phone, a smart watch, a tablet, a cell phone, a single board computer, a laptop computer, a desktop computer, or a cloud server computer. The software may compute the metrics automatically or allow a user to generate metrics based on customized requirements. An exemplary embodiment of the analysis module is illustrated in FIG. 11, which depicts the software allowing customized metric generation.

It is to be understood that the terms "including", "comprising", "consisting" and grammatical variants thereof do not preclude the addition of one or more components, features, steps, or integers or groups thereof and that the terms are to be construed as specifying components, features, steps or integers. If the specification or claims refer to "an additional" element, that does not preclude there being more than one of the additional element. It is to be understood that where the claims or specification refer to "a" or "an" element, such reference is not be construed that there is only one of that element. It is to be understood that where the specification states that a component, feature, structure, or characteristic "may", "might", "can" or "could" be included, that particular component, feature, structure, or characteristic is not required to be included.

Thus, the embodiments of the present disclosure are well adapted to carry out the objects and attain the ends and advantages mentioned above as well as those inherent therein. While the inventive device and system have been described and illustrated herein by reference to particular non-limiting embodiments in relation to the drawings attached thereto, various changes and further modifications, apart from those shown or suggested herein, may be made therein by those of ordinary skill in the art, without departing from the spirit of the inventive concepts.

What is claimed is:

1. A toe dynamometer comprising:
   a platform configured to accommodate a patient's foot; and
   a sensor assembly comprising a force sensor and a toe cap connected to the force sensor, wherein the force sensor is configured to measure forces applied to the force sensor by toe flexion on the force sensor and from toe extension away on the force sensor through the toe cap.

2. The toe dynamometer of claim 1, wherein the sensor assembly is contained within the platform such that the force sensor is substantially flush with the surface of the platform.

3. The toe dynamometer of claim 1, wherein the force sensor is configured to measure and produce output signals representative of the magnitude and direction of the forces applied by toe flexion and toe extension over time.

4. The toe dynamometer of claim 3, further comprising a control module that is configured to record, process and store the output signals produced by the force sensor.

5. The toe dynamometer of claim 1, wherein the toe cap is adjustable.

6. The toe dynamometer of claim 1, further comprising a patient display module that is configured to visually report to the patient in real-time the forces measured by the sensor assembly.

7. The toe dynamometer of claim 6, wherein the patient display module is further configured to play a series of instructive audio recordings to the patient during a measurement session.

8. The toe dynamometer of claim 1, further comprising a control module connected to the sensor assembly, wherein the control module includes an output module selected from the group consisting of a display, a removable memory card slot, a printer, a wired data port, and a wireless network adapter.

9. A toe dynamometer comprising:
   a platform configured to accommodate a patient's foot;
   a sensor assembly comprising a force sensor and a toe cap connected to the force sensor, wherein the force sensor is configured to measure forces applied to the force sensor by toe flexion on the force sensor and from toe extension away on the force sensor through the toe cap; and
   a control module connected to the sensor assembly.

10. The toe dynamometer of claim 9, wherein the control module includes an output module selected from the group consisting of a display, a removable memory card slot, a printer, a wired data port, and a wireless network adapter.

11. The toe dynamometer of claim 9, wherein the sensor assembly is contained within the platform such that the force sensor is substantially flush with the surface of the platform.

12. The toe dynamometer of claim 9, wherein the force sensor is configured to measure and produce output signals representative of the magnitude and direction of the forces applied by toe flexion and toe extension over time.

13. The toe dynamometer of claim 12, wherein the control module is configured to record, process and store the output signals produced by the force sensor.

14. The toe dynamometer of claim 9, wherein the force sensor is configured to measure and produce output signals representative of the magnitude and direction of the forces applied by toe flexion and toe extension over time.

15. A method for measuring a patient's toe strength with a toe dynamometer during a measurement session, the method comprising the steps of:
   securing the patient's toe within a sensor assembly on the toe dynamometer where the sensor assembly has a force sensor and a toe cap connected to the force sensor, where the force sensor is under the patient's toe and the toe cap is above the patient's toe;
   instructing the patient to execute an examination protocol that includes toe flexion maneuvers, toe extension maneuvers, or a combination of toe flexion and toe extension maneuvers; and
   recording in real time the force measurements resulting from the application of force by the patient's toe on the force sensor during the examination protocol.

16. The method of claim 15 further comprising the step of:
   securing a foot of the patient to the toe dynamometer with a foot strap.

17. The method of claim 16, wherein the step of securing the foot of the patient to the toe dynamometer further comprises strapping the patient's foot to the toe dynamometer.

18. The method of claim 15, further comprising the step of outputting the force measurement data to a computer connected to the toe dynamometer.

19. The method of claim 15, further comprising the step of analyzing the recorded force measurements to determine metrics about the patient's health.

20. The method of claim 19, wherein the step of analyzing the recorded force measurements further comprises analyzing force measurements over time to determine a metric selected from the group consisting of peak strength, time to peak strength, rate of force increase to peak strength, rate of force decrease after peak strength, and degree of unsteadiness in strength profile.

* * * * *